United States Patent
Brittain et al.

(10) Patent No.: US 8,072,593 B2
(45) Date of Patent: Dec. 6, 2011

(54) METHOD AND APPARATUS FOR ILLUMINATING MATERIAL FOR AUTOMATED INSPECTION

(75) Inventors: Kenneth G. Brittain, Cottage Grove, MN (US); Steven P. Floeder, Shoreview, MN (US)

(73) Assignee: 3M Innovative Properties Company, St. Paul, MN (US)

(*) Notice: Subject to any disclaimer, the term of this patent is extended or adjusted under 35 U.S.C. 154(b) by 948 days.

(21) Appl. No.: 12/017,156

(22) Filed: Jan. 21, 2008

(65) Prior Publication Data

US 2008/0198602 A1    Aug. 21, 2008

Related U.S. Application Data

(60) Provisional application No. 60/890,284, filed on Feb. 16, 2007.

(51) Int. Cl.
*G01N 21/00* (2006.01)

(52) U.S. Cl. .................. 356/239.7; 356/239.1

(58) Field of Classification Search .......... None
See application file for complete search history.

(56) References Cited

U.S. PATENT DOCUMENTS

| | | | |
|---|---|---|---|
| 5,132,791 A | 7/1992 | Wertz et al. | |
| 5,172,005 A | 12/1992 | Cochran et al. | |
| 5,847,834 A | 12/1998 | Ho et al. | |
| 6,011,620 A * | 1/2000 | Sites et al. | 356/239.1 |
| 6,170,973 B1 | 1/2001 | Benedict | |
| 6,207,946 B1 * | 3/2001 | Jusoh et al. | 250/208.1 |
| 6,437,357 B1 * | 8/2002 | Weiss et al. | 356/430 |
| 7,230,229 B2 | 6/2007 | Gerard et al. | |
| 7,369,240 B1 * | 5/2008 | Abbott et al. | 356/430 |
| 7,880,156 B2 * | 2/2011 | Shakespeare | 250/559.4 |
| 2003/0189704 A1 | 10/2003 | Floeder et al. | |
| 2005/0075801 A1 | 4/2005 | Skeps et al. | |
| 2005/0141760 A1 | 6/2005 | Floeder et al. | |
| 2005/0232475 A1 | 10/2005 | Floeder et al. | |

FOREIGN PATENT DOCUMENTS

GB    2 157 824    10/1985

* cited by examiner

*Primary Examiner* — Gregory J Toatley
*Assistant Examiner* — Juan D Valentin
(74) *Attorney, Agent, or Firm* — Steven A. Bern; Scott A. Baum

(57) ABSTRACT

A lighting configuration that is a combination of far dark field lighting and a modified dark stripe lighting is disclosed. The novel combination provides a more robust detection of flaws on, e.g. a moving web of transparent film, than either would provide alone or through a summation of their individual parts.

12 Claims, 7 Drawing Sheets

METHOD AND APPARATUS FOR ILLUMINATING MATERIAL FOR AUTOMATED INSPECTION

CROSS REFERENCE TO RELATED APPLICATION

This application claims the benefit of U.S. Provisional Patent Application No. 60/890,284, filed Feb. 16, 2007, the disclosure of which is incorporated by reference herein in its entirety.

TECHNICAL FIELD

The present disclosure is related to machine vision, and more particularly to the illumination of transparent or semi-transparent materials so as to maximize the detection and recognition of flaws.

BACKGROUND

In recent years, with the assistance of capable computing, it has been possible to use automated equipment to perform some of the inspection tasks that previously required a human eye. Such "machine vision" techniques have become more sophisticated, and among other things have been employed for the inspection of sheets and webs of material. Good illumination of the article being inspected is needed for the proper deployment of machine vision, especially when inspecting for surface defects on transparent or semi-transparent webs.

One technique that has been employed is the so called, "far dark field" technique, which is used to detect defects that strongly scatter light. When using the far dark field technique, one or two light sources are placed so that their light falls upon the article to be inspected (for example, a film or similar material) at an angle to the line of vision of the camera. In the absence of an upset condition, e.g. a defect, the camera will normally see no light from these sources. Only when a surface defect passes through the beams will light be reflected toward the camera so that flaws are seen as lighted areas on a normally dark image.

Another technique is the so called, "dark stripe" technique, which is used to detect defects that weakly scatter or deflect light. When using the dark stripe technique, illumination from a source is aimed through the web and directly at the camera. This illumination is diffused and attenuated with a dark stripe mask. This mask is intended to block the majority of diffuse light from the view of the camera. Only when a surface defect that reflects or refracts the light rays from their indirect paths will light be diverted towards the camera so that flaws are seen as lighted areas on a normally dark image.

Each has some advantages for highlighting the flaws on clear webs, but there are some defects that resist detection with one or the other of these methods.

SUMMARY

In one exemplary respect, the disclosure is directed to an illumination system for illuminating a transparent, or semi-transparent, or a combination thereof, material for inspection by an optical receiving device, e.g., a camera. The system includes a direct source for providing light on the material in the direction of the camera, and a dark stripe positioned between the direct source and the camera. There will also be at least a first, and in some embodiments a second, dark field source, for providing light on the transparent material at an angle to the camera. When a second dark field source is present, it provides light on the material at a different angle from the camera than is provided by the first dark field source. It is particularly convenient to construct the system so that the direction of illumination of the dark stripe source is normal to the plane of the transparent sheet material. In some embodiments cases, results are achieved when the angle between the direction of illumination of the first dark field source is at an angle of between about 10 to 50 degrees from normal to the plane of the inspected material, though this is not essential. If a second dark field source is present, the angle between the direction of illumination of the second dark field source is also preferably at an angle of between about 10 to 50 degrees from normal to the plane of the transparent sheet material, although in a different way than the first dark field source, though this is not essential.

In some embodiments, a lens is positioned between the first and the second dark field sources and the material. In some embodiments, it is particularly convenient to provide the first and the second dark field sources as fiber light lines and the lenses are conveniently provided as cylindrical lenses. As will be discussed with more particularity below, it is the teaching of this disclosure that the dark strip associated with the direct source can be significantly narrower than those presently employed by the art. Good results are achieved in connection with the disclosed combination when the width of the dark stripe is between about 1.0 and 2.5 mm, though this range is not essential.

DESCRIPTION OF THE DRAWING

FIG. 4b shows a screen print of a computer generated graph of the light intensity of a horizontal section of the image of FIG. 4a.

DETAILED DESCRIPTION

Applicants have discovered that a lighting configuration can be prepared that provides the advantages of the far dark field and dark stripe techniques as a single station monitored by a single imaging camera. More specifically, provided is a lighting configuration that is a combination of far dark field lighting and a modified dark stripe lighting, and the novel combination provides a unexpectedly more robust detection of flaws than either would provide alone. Each of these two approaches highlights different aspects of each defect. On their own, they cannot create a reliable signal contrast for certain defects. However, when optically combined, they create excellent contrast of small surface defects beyond that which can be achieved by summing their respective images together in a post processing method. Portions of defects that may be only marginally detectable with either single approach become enhanced and to the point that they are visible and readily detectable.

Figure 1:
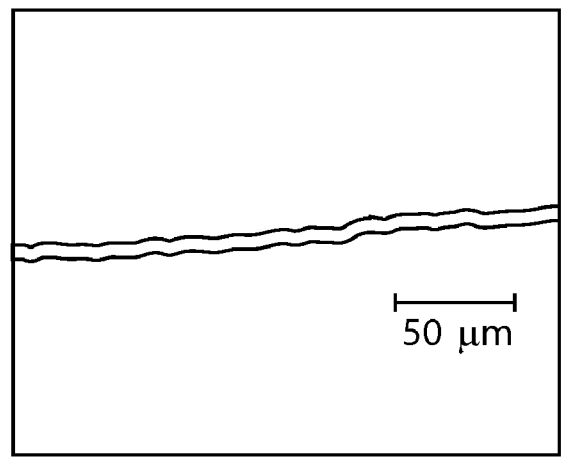
FIG. 1 shows a photomicrograph of representative small defect in a coated optical film.
Figure 2:
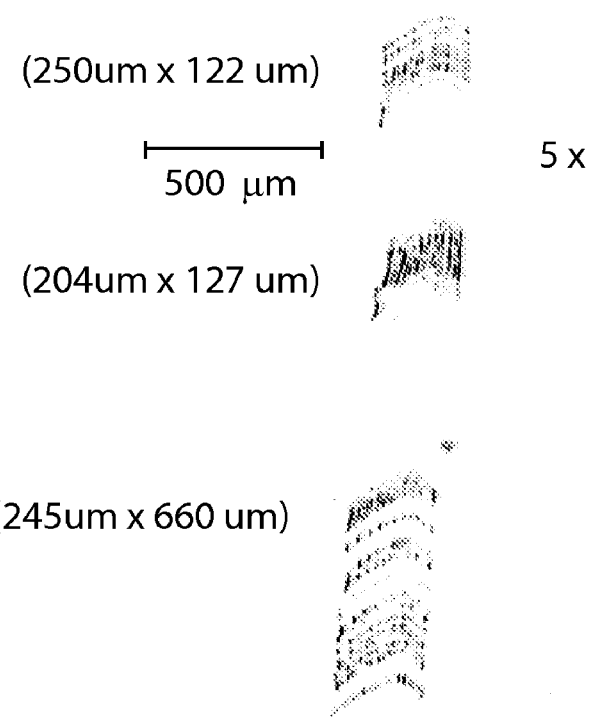
FIG. 2 shows a photomicrograph of a representative large defect in a coated optical film.

Referring now to FIG. 1, a photomicrograph of typical small defect in a coated optical film is provided. This sort of defect may arise due to a fine scratch in the substrate. In contrast, FIG. 2 shows a rather larger defect of a type that can be caused by, e.g. a coating upset. Previously known illumination systems can be selected to discern one or the other, but are inefficient when both types of defects are present.

Figure 3A:
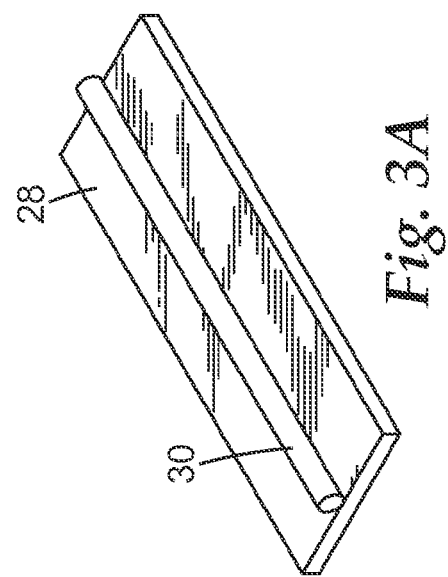
FIG. 3a shows a dark stripe above a diffuser.
Figure 3:
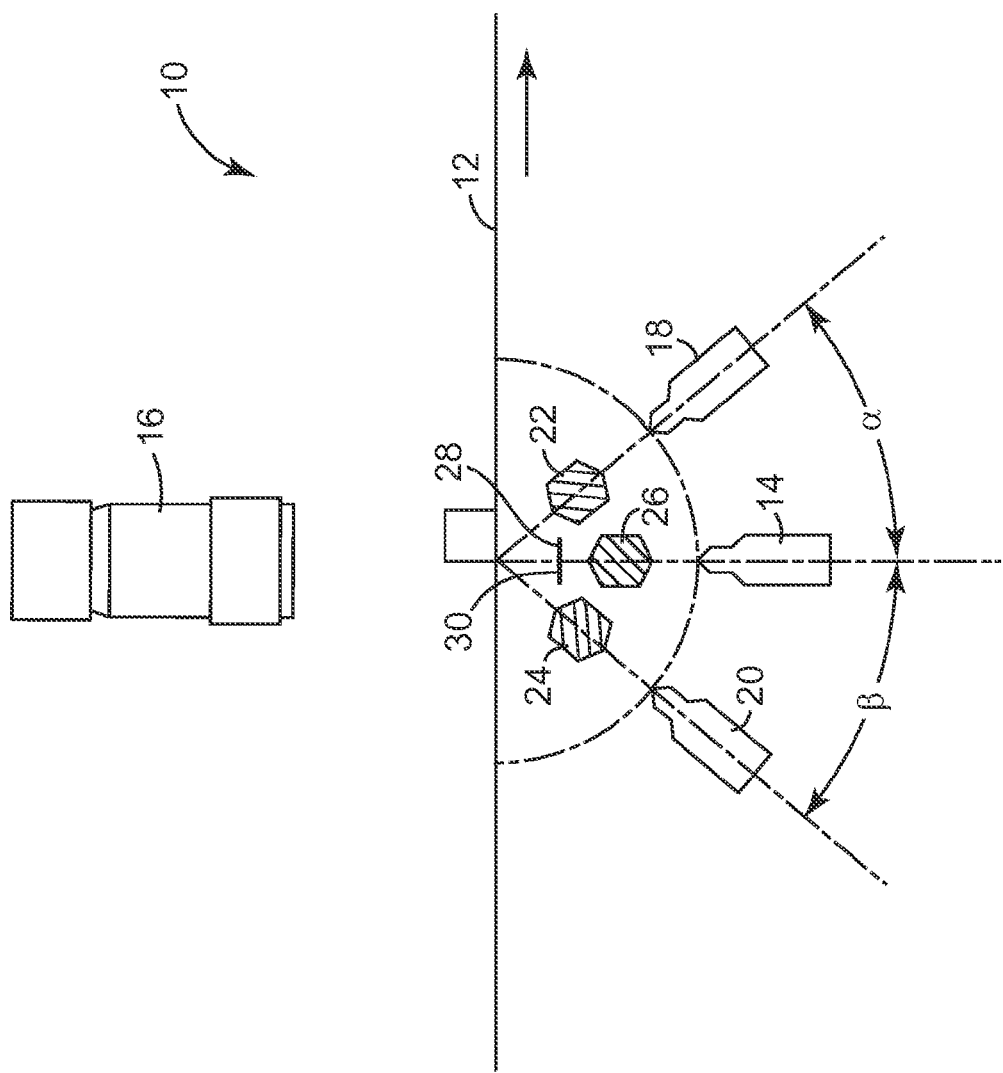
FIG. 3 shows a schematic side view of a machine vision station equipped with an illumination system according to the present disclosure.

Referring now to FIG. 3, a schematic view of an exemplary illumination system 10 according to the present disclosure is illustrated. The illumination system 10 is shown in side view with respect to the direction of travel (arrow) of a moving web 12 of material which is typically of indefinite length. It should be noted that the illumination system is suitable for inspecting other product forms such as discrete sheets of transparent (or semi-transparent) material.

The illumination system 10 includes at least two, or in some embodiments, three light sources. The direct source 14 shines light in the direction of a camera 16. The far dark field sources 18 and 20 shine their light at an angle ($\alpha+\beta$, respectively) to the camera 16. Most conveniently, the direct source 14 is positioned to illuminate in a direction normal to the plane of the web 12. In some embodiments, the source is conveniently provided as a fiber light line or as a fluorescent lamp illuminating a strip across an entire width of the web 12. While it is convenient to orient this strip parallel to the cross web direction, this is not believed to be essential.

The dark field sources 18 and 20 also, can be conveniently provided as fiber light lines, although a laser source or other source may be employed. The dark field sources 18 and 20 conveniently illuminate a strip across the entire width of the web 12, oriented along the cross web direction. However, in some embodiments, they are mounted at an angle to the direction normal to the plane of the web 12. An angle of about 25 degrees from the normal direction is believed to be most advantageous, though not essential.

In some embodiments, lenses are used to focus the light emerging from the direct sources and the two dark field sources. For example, when fiber light lines are used as the sources, cylindrical lenses oriented parallel to the fiber light lines may be used. The cylindrical lenses 22 and 24 preferably focus the light from far dark field sources 18 and 20 onto the underside of the web 12 on a line directly under the camera 16. The cylindrical lens 26 that focuses light from direct source 14 can have the same focal length as cylindrical lenses 22 and 24, but the light from the direct source is directed onto a diffuser 28. A solid object, for example a taut cable or narrow piece of metal, is mounted just above (or on) the diffuser 28 to provide a dark stripe 30 as shown in FIG. 3a. In some embodiments, the dark stripe 30 is preferably very dark, which can, for example, be conveniently employed by using a cable that has carbon black colored insulation. It is within the knowledge of one skilled in the art to select a suitable object to create dark stripe for a given application.

As will be discussed with more particularity below, it has been discovered that in the combination of elements provided by the present disclosure, the most suitable dark stripe is much narrower than that which would be used by artisans familiar with optical inspection, when confronted with a situation calling for what the art presently knows as "dark stripe illumination", which traditionally requires a dark stripe significantly larger than the camera array. It has been found that a dark stripe having a width of between about 0.04 and 0.10 inch (1.0 to 2.5 mm) provides very good results in connection with the present disclosure. While not wishing to be bound by any theory, it is believed that the narrower width, approaching the width of the camera array, recruits a diffraction phenomenon to the aid of the robust detection of defects. Regardless, a system with a stripe much wider than the listed range may suffer a significant decrease in the ability to detect fine scratches. A system with a stripe much narrower than the listed range may cause the camera to saturate at all useable light output levels from the direct source.

Figure 4A:
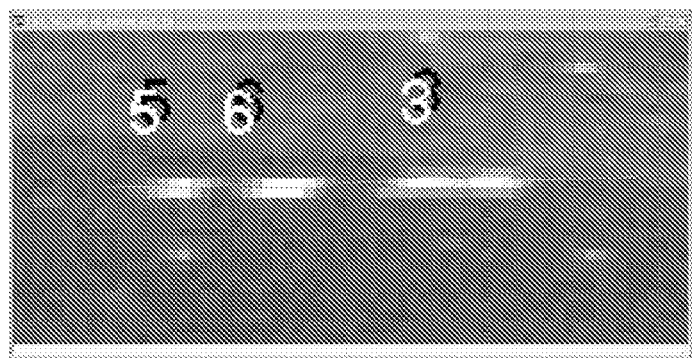
FIG. 4a shows a screen print of a computer capture of a camera image of a mixed type defect illuminated with only a far dark field illumination.

Referring now to FIG. 4a, a screen print of a computer capture of a camera image of a mixed type defect on a transparent coated film illuminated with only a far dark field illumination is illustrated. The computer has assigned arbitrary reference numerals "5" "6", and "3" left to right to three detected anomalies. A screen print of a computer generated graph of the light intensity along a horizontal section of the image of FIG. 4a which intersects the tagged defects is provided in FIG. 4b. It will be observed in this graph that the twin peaks on the right side of the graph that correspond to anomaly "5" are very shallow compared to the baseline. The detection of this anomaly is far from robust for many purposes.

Figure 4C:
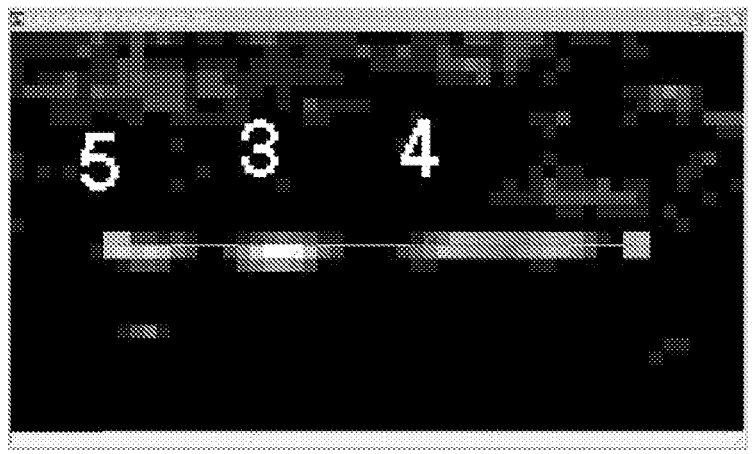
FIG. 4c shows a screen print of a computer capture of a camera image of the defect of FIG. 4a, this time illuminated with only a dark stripe illumination.

Referring now to FIG. 4c, a screen print of a computer capture of a camera image of the same group of anomalies depicted in FIG. 4a is presented, except that for this creation of image only a dark stripe illumination was used. Once again, the computer has assigned arbitrary reference numerals to three detected anomalies, this time "5", "3", and "4" left to right. A screen print of a computer generated graph of the light intensity along a horizontal section of the image of FIG. 4c is provided in FIG. 4d. It is the same horizontal section that was analyzed in FIG. 4b. It is observed in this graph that the twin peaks on the right side of the graph that in this Figure correspond to anomaly "4" are very shallow compared to the baseline. The detection of this anomaly is still far from robust for many purposes.

Figure 4E:
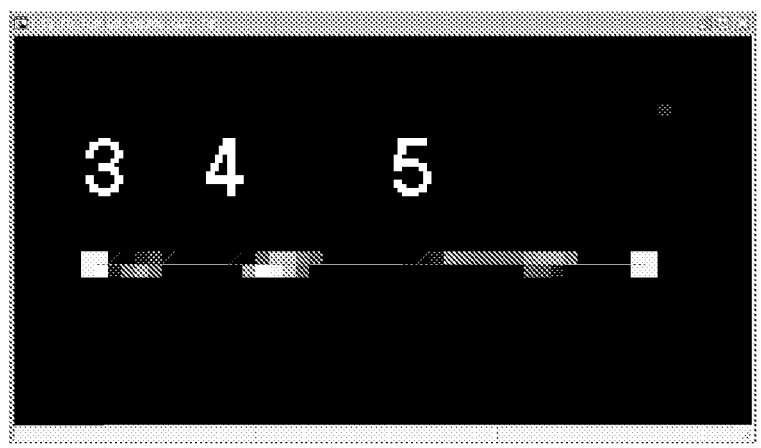
FIG. 4e shows a screen print of a computer capture of a camera image of the defect of FIG. 4a, this time illuminated with an illumination system of the present disclosure as illustrated in FIG. 3.
Figure 4B:
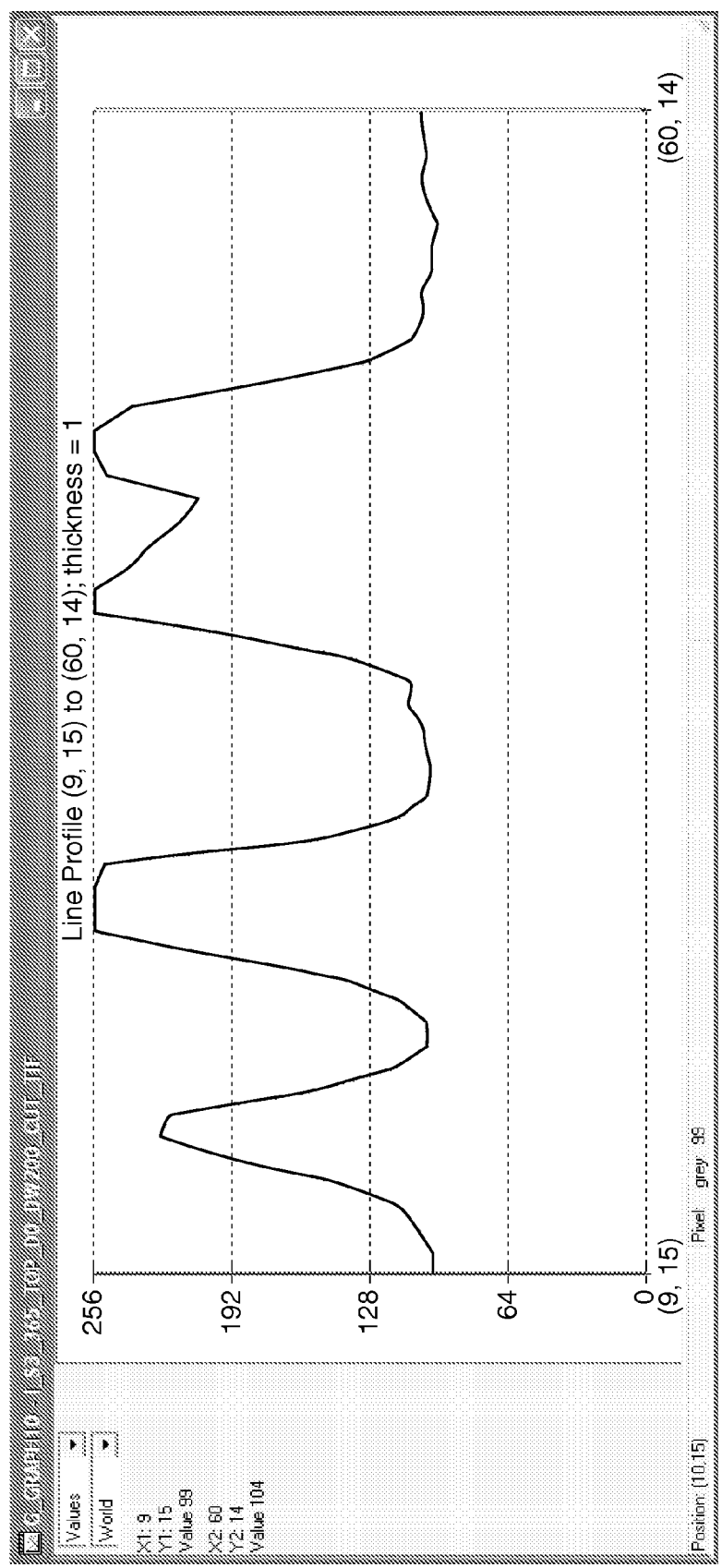
Figure 4D:
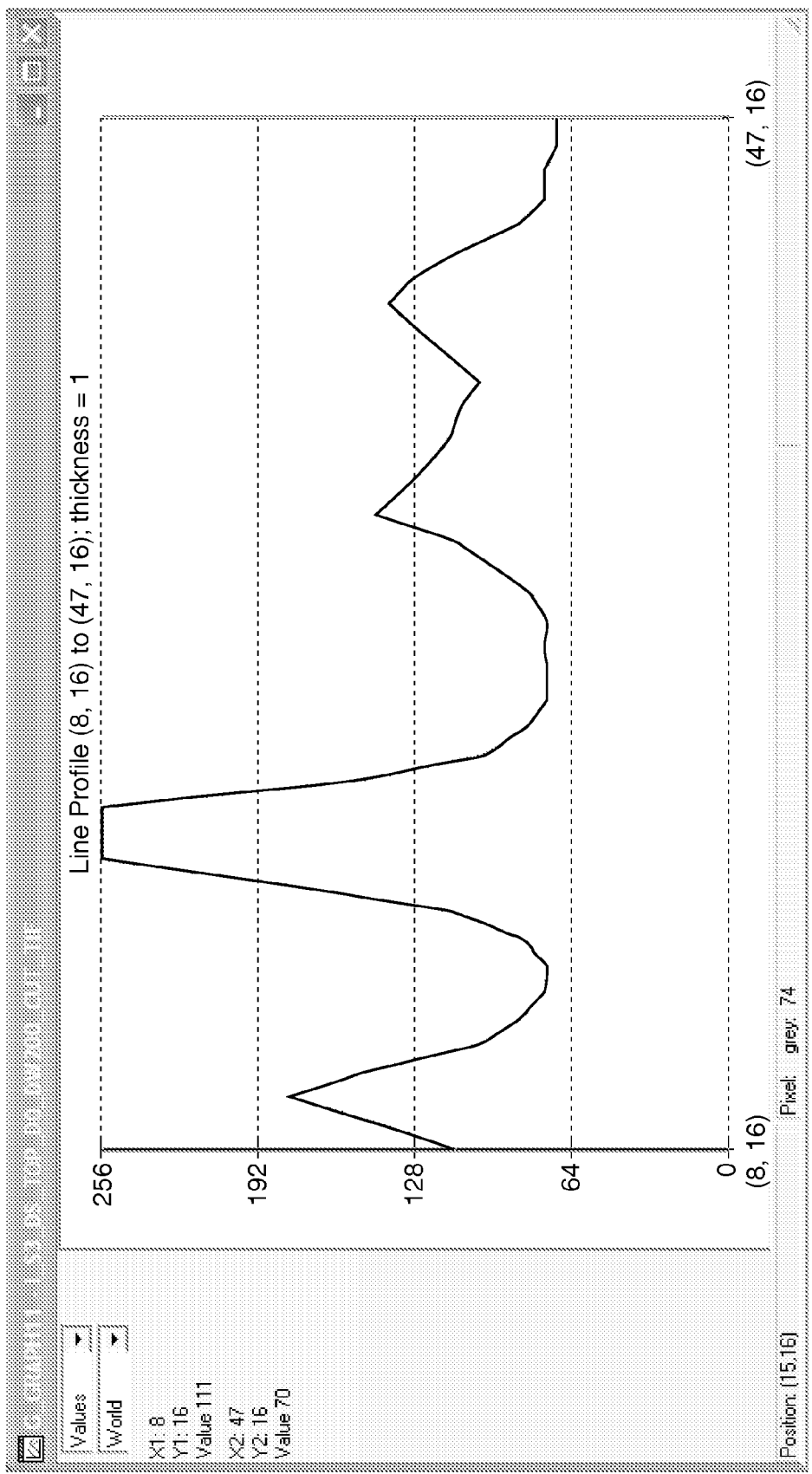
FIG. 4d shows a screen print of a computer generated graph of the light intensity of image 4c along the same horizontal section used in of the image of 4b.
Figure 4F:
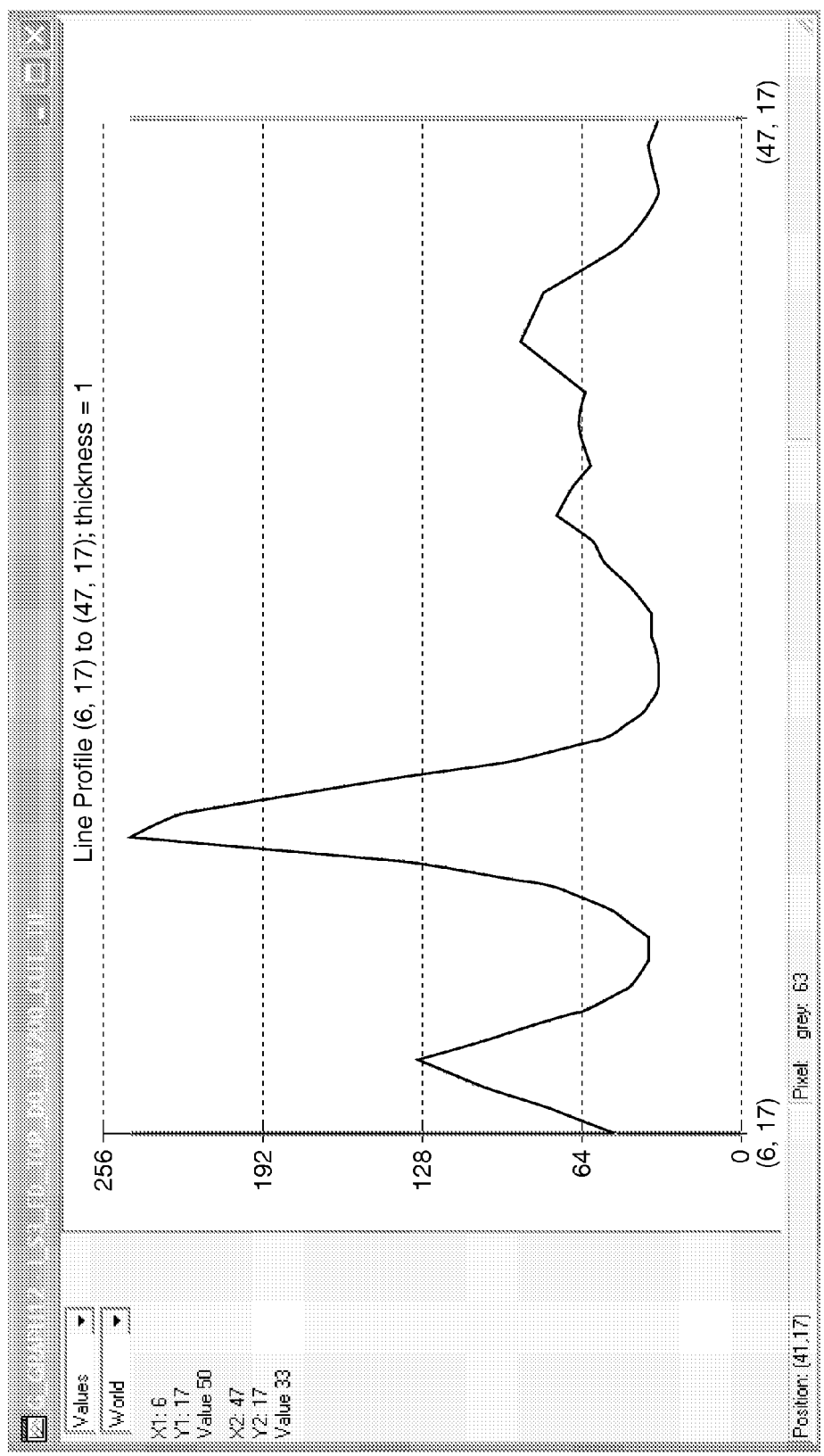
FIG. 4f shows a screen print of a computer generated graph of the light intensity of image 4e along the same horizontal section used in of the image of 4b.

Referring now to FIG. 4e, a screen print of a computer capture of a camera image of the same group of anomalies depicted in FIG. 4a is presented, except that for this Figure an illumination system according to the present disclosure a generally configured according to FIG. 3 was used. Once again, the computer has assigned arbitrary reference numerals to three detected anomalies, this time "3", "4", and "5" left to right. A screen print of a computer generated graph of the light intensity along a horizontal section of the image of FIG. 4e is provided in FIG. 4f. It is the same horizontal section that was analyzed in FIG. 4b. In this graph, it can readily be appreciated how robust the detection of anomalies has become with the illumination system of the present disclosure. The contrast between the intensity peaks and the baseline is very sharp and distinct for all the detected anomalies. It is clear that the impact of the innovative illumination system is much more than additive, and provides a substantial synergy.

Example

A web inspection station was constructed generally as depicted in FIG. 1. The illumination system was mounted below the web path of a conventional web-handling system on a free span between idler rollers. An AVIIVA™ CCD monochrome linescan camera, commercially available from Atmel of San Jose, Calif., equipped with a conventional 150 mm lens, was mounted above illumination system, 83 cm above the web path. The illumination system included three light sources, each included a fiber light line commercially available from Fostec Imaging of San Diego, Calif., driven by a Model 4900 Auto-Calibrating Light Source commercially available from Illumination Technologies of East Syracuse, N.Y. The direct source was aimed directly upwards towards the camera, while the two far dark field sources were aimed at an angle 40 degrees from the vertical. All three sources were otherwise oriented with their long axes parallel to the cross web direction.

Each of the three sources was provided with a cylindrical lens, each made from optically clear acrylic polymer, 1.25 inch (31.75 mm) in diameter. An aluminum frame having a 0.5 inch (12.5 mm) wide slot was mounted between the direct source and the underside of the web such that light from the direct source passed through one of the cylindrical lenses and then through the slot on its way to the underside of the web. A translucent film of matte finished diffuser was placed across the top of the slot. Immediately above that, a steel cable was mounted to the frame so as to provide a dark stripe along the long axis of the slot. The cable was 0.094 inch (2.38 mm) in diameter, and was coated with dark black insulation.

The output of the camera was directed to a personal computer for analysis. This computer was running the Matrox Inspector 2.2 software package, commercially available from Matrox Imaging of Dorval, Quebec, Canada. Other background information about analyzing the information stream from a camera for the identification of defects can be found in coassigned U.S. Patent Application Publication No. 20050075801, "Apparatus And Method For Automated Web Inspection", to Skeps, et al. Additional background information is disclosed in coassigned U.S. Patent Application Publication No. 20050141760, "Maximumization of Yield for Web-based Articles," Floeder et al. Both are incorporated by reference as if re-written.

The web inspection station was used to inspect 7 mm thick optical quality clear polyester film of the sort that might be used in the manufacture of a variety of products. The particular roll of material for the experiment was chosen because it showed a variety of possible flaws, all the way from gross defects like gouges and surface contamination with sizes ranging from one to several hundred microns, to very fine scratches with widths of approximately 15 to 20 microns.

Figure 5:
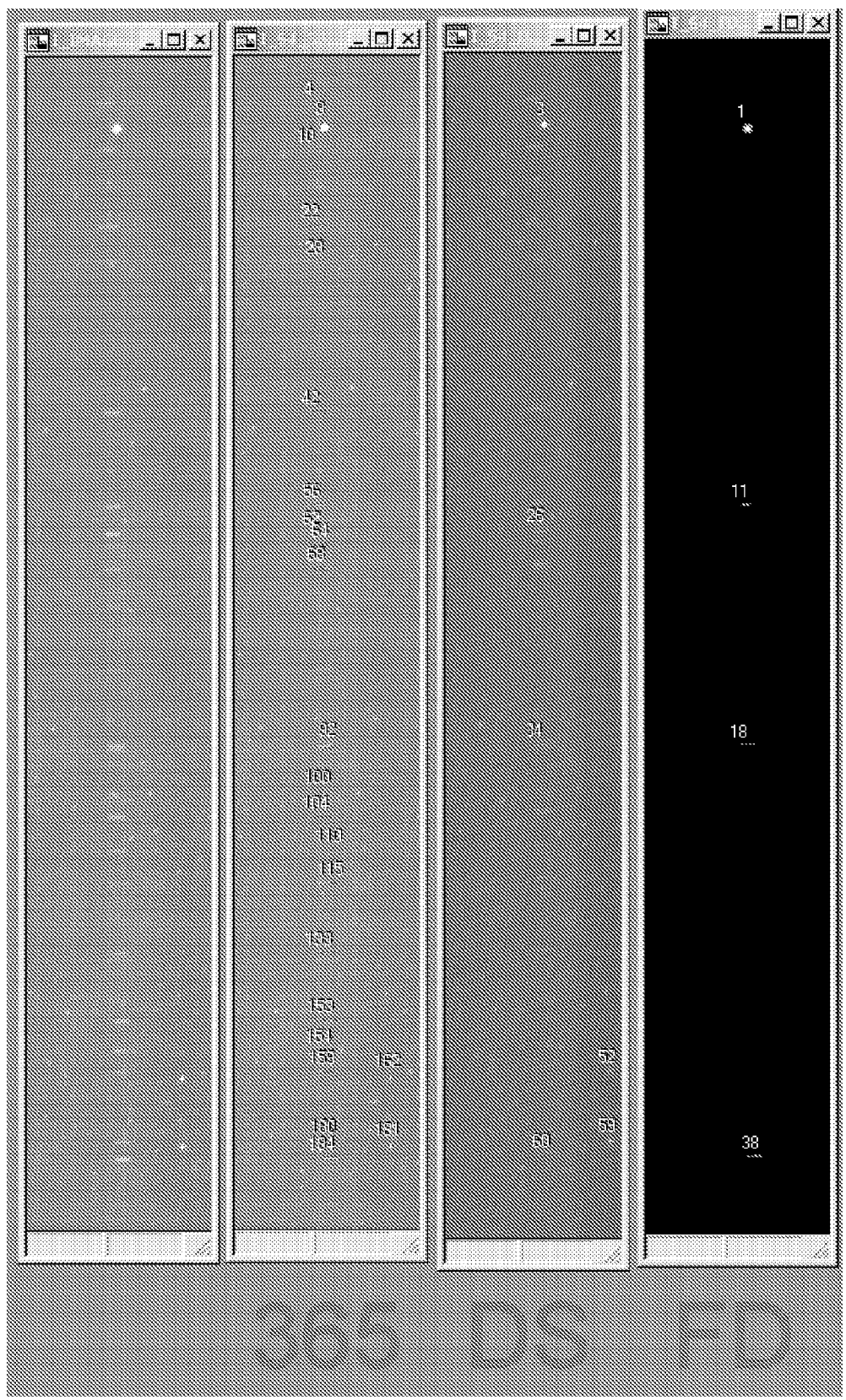
FIG. 5 shows a screenprint of a computer screen displaying four passes of the same portion of a test web by the illumination system of a type shown in FIG. 3.

In FIG. 5, a screenprint of the computer screen is presented, with four passes of the same portion of the web arranged side by side. The third column is an experimental pass with only the direct source turned on so that the film is illuminated with only modified dark stripe illumination. The detected flaws are arbitrarily enumerated by the computer's program. The fourth column is an experimental pass with only the two dark field sources turned on so that the film is illuminated with only modified dark field illumination. Again the detected flaws are arbitrarily enumerated. The first column and the second columns are different presentations of an experimental pass with all three sources turned on according to the teaching of the present disclosure. In the first column the enumeration of the flaws has been suppressed so that the raw image can be better viewed. It will be appreciated from the preceding that there is a significant synergistic effect associated with the illumination system of the present disclosure: the system noted not only all the flaws that the more conventional illumination methods used standing alone did, but other, less distinguishable flaws as well. Furthermore, the system accomplishes the task of illuminating flaws for detection with no increase in sensors or processing equipment, thereby enabling simpler inspection systems to have higher performance While the invention has been particularly shown and described with reference to various embodiments thereof, it will be understood by those skilled in the art that various other changes in the form and details may be made therein without departing from the spirit and scope of the invention.

What is claimed is:

1. A system for illuminating a transparent, or semi-transparent, or a combination thereof, sheet material for inspection by an optical receiving device, comprising:
   a direct source located on one side of the sheet material for providing light on the sheet material in the direction of a camera located on the opposite side of the sheet material and a diffuser located between the direct source and the sheet material;
   a dark stripe positioned between the diffuser and the sheet material;
   at least a first dark field source, located on the same side of the sheet material as the direct source, for providing light on the transparent sheet material at an angle to the direct source.

2. The illumination system according to claim 1 further comprising a second dark field source for providing light on the sheet material at a different direction from the direct source than provided by the first dark field source.

3. The illumination system according to claim 2 wherein the direction of illumination of the direct source is normal to the plane of the sheet material.

4. The illumination system according to claim 3 wherein the angle between the direction of illumination of the first dark field source is at an angle of between about 10 to 50 degrees from normal to the plane of the sheet material.

5. The illumination system according to claim 4 wherein the angle between the direction of illumination of the second dark field source is at an angle of between about 10 to 50 degrees from normal to the plane of the sheet material.

6. The illumination system according to claim 5 further comprising a lens positioned between the first and the second dark field sources and the sheet material.

7. The illumination system according to claim 6 wherein the first and the second dark field sources are fiber light lines, and further wherein the lenses are cylindrical lenses.

8. The illumination system according to claim 1 wherein a width of the dark stripe is 0.04 to 0.10 inch.

9. The illumination system according to claim 1 wherein the direct source is a fluorescent source, an LED source, or a source coupled to a fiber-optic device.

10. A method for illuminating a transparent, or semi-transparent, or a combination thereof, sheet material and inspecting it for anomalies comprising:
    providing a direct source located on one side of the sheet material illuminating the sheet material in the direction of a camera located on the opposite side of the sheet material and providing a diffuser located between the direct source and the sheet material;
    providing a dark stripe positioned between the diffuser and the sheet material;
    providing at least a first dark field source, located on the same side of the sheet material as the direct source, and illuminating the sheet material at an angle to the direct source; and
    analyzing the output of the camera to detect anomalies in the sheet material.

11. The method according to claim 10 further comprising providing a second dark field source for illuminating the sheet material in a different direction relative to the direct source than provided by the first dark field source.

12. The method of claim 11 wherein the analyzing comprises using a software package.

* * * * *

UNITED STATES PATENT AND TRADEMARK OFFICE
CERTIFICATE OF CORRECTION

| | | |
|---|---|---|
| PATENT NO. | : 8,072,593 B2 | Page 1 of 1 |
| APPLICATION NO. | : 12/017156 | |
| DATED | : December 6, 2011 | |
| INVENTOR(S) | : Kenneth G Brittain et al. | |

It is certified that error appears in the above-identified patent and that said Letters Patent is hereby corrected as shown below:

Column 5
Line 38, delete ""Maximumization" and insert -- "Maximization --, therefor.

Column 6
Line 4, delete "performance" and insert -- performance. --, therefor.
Line 24, in Claim 1, after "the" delete "transparent".

Signed and Sealed this
Seventh Day of February, 2012

David J. Kappos
*Director of the United States Patent and Trademark Office*